(12) United States Patent
Kinjo et al.

(10) Patent No.: US 9,546,363 B2
(45) Date of Patent: Jan. 17, 2017

(54) METHOD FOR STABILIZING ASCORBIC ACID OXIDASE

(71) Applicant: KYOWA MEDEX CO., LTD., Chuo-ku, Tokyo (JP)

(72) Inventors: Kenta Kinjo, Sunto-gun (JP); Tomoko Aratake, Sunto-gun (JP)

(73) Assignee: KYOWA MEDEX CO., LTD., Tokyo (JP)

( * ) Notice: Subject to any disclaimer, the term of this patent is extended or adjusted under 35 U.S.C. 154(b) by 0 days.

(21) Appl. No.: 14/399,983

(22) PCT Filed: May 23, 2013

(86) PCT No.: PCT/JP2013/064387
§ 371 (c)(1),
(2) Date: Nov. 10, 2014

(87) PCT Pub. No.: WO2013/176225
PCT Pub. Date: Nov. 28, 2013

(65) Prior Publication Data
US 2015/0147798 A1    May 28, 2015

(30) Foreign Application Priority Data
May 25, 2012  (JP) ................................. 2012-119582

(51) Int. Cl.
*C12N 9/96*    (2006.01)
*C12N 9/00*    (2006.01)
*C12N 9/02*    (2006.01)

(52) U.S. Cl.
CPC ............... *C12N 9/96* (2013.01); *C12N 9/0063* (2013.01); *C12Y 110/03003* (2013.01)

(58) Field of Classification Search
None
See application file for complete search history.

(56) References Cited

FOREIGN PATENT DOCUMENTS

| | | |
|---|---|---|
| JP | 63-049081 | 3/1988 |
| JP | 04-066087 | 3/1992 |
| JP | 05-244948 | 9/1993 |
| JP | 06-062846 | 3/1994 |
| JP | 8-15430 | 2/1996 |
| JP | 2002-233363 | 8/2002 |
| JP | 2003-116539 | 4/2003 |
| JP | 2004-105025 | 4/2004 |
| JP | 2005-114368 | 4/2005 |
| JP | 2007-228842 | 9/2007 |
| JP | 2013-074876 | 4/2013 |
| JP | 2013-074877 | 4/2013 |
| WO | 2011/126067 | 10/2011 |

OTHER PUBLICATIONS

Munyaka, et al., "Thermal Stability of L-Ascorbic Acid and Ascorbic Acid Oxidase in Broccoli", Journal of Food Science, vol. 75, No. 4 (2010) C336-40.
Powers, et al., "On the Inactivation of Ascorbic Acid Oxidase", The Journal of General Physiology (1943) 181-99.

*Primary Examiner* — Suzanne M Noakes
(74) *Attorney, Agent, or Firm* — Fitzpatrick, Cella, Harper & Scinto

(57) ABSTRACT

Provided are: a method for stabilizing an ascorbic acid oxidase; a method for preserving an ascorbic acid oxidase; and a stabilized composition of an ascorbic acid oxidase. A method for stabilizing an ascorbic acid oxidase and a method for preserving an ascorbic acid oxidase, each of the methods comprising allowing an ascorbic acid oxidase to coexist with nitrous acid or a salt thereof, or a nitrous acid ester in an aqueous medium; and a stabilized composition of an ascorbic acid oxidase, which comprises an ascorbic acid oxidase being allowed to coexist with nitrous acid or a salt thereof, or a nitrous acid ester in an aqueous medium. The method for stabilizing an ascorbic acid oxidase, the method for preserving an ascorbic acid oxidase, and the stabilized composition of an ascorbic acid oxidase according to the present invention are useful for clinical diagnosis and the like.

2 Claims, No Drawings

METHOD FOR STABILIZING ASCORBIC ACID OXIDASE

This application is a National Phase of PCT/JP2013/064387 filed May 23, 2013, which in turn claims benefit JP 2012-119582 filed May 25, 2012.

TECHNICAL FIELD

The present invention relates to a method for stabilizing an ascorbic acid oxidase and a stabilized composition of an ascorbic acid oxidase.

BACKGROUND ART

A clinical test is routinely carried out which involves converting a component to be measured in a biological sample, such as serum, into hydrogen peroxide using an oxidase and measuring the generated hydrogen peroxide to determine the component to be measured. There is often a problem of the influence of interfering substances, such as ascorbic acid and bilirubin, contained in a biological sample, in a method for measuring a component to be measured in the biological sample based on the measurement of hydrogen peroxide. Particularly, ascorbic acid has an extremely strong reduction effect; to avoid the influence thereof, a method involving converting ascorbic acid to dehydroascorbic acid using an ascorbic acid oxidase to suppress the influence of ascorbic acid is often used in a clinical test.

Ascorbic acid oxidase is a blue copper protein having a molecular weight of about 140,000 and converts ascorbic acid to dehydroascorbic acid. To suppress the influence of ascorbic acid, an ascorbic acid oxidase is often contained in a reagent for measuring a component to be measured in a biological sample. However, there is a problem that an ascorbic acid oxidase is unstable and is deactivated during the preservation of the reagent to deteriorate the performance of the reagent.

Against the problem, there are known a method for stabilizing an ascorbic acid oxidase by adding a compound having both of a metal or a positive basic group and a negative acid group, or a combination of the compound, catalase and/or peroxidase, and an oxidative dye coupler to a solution containing an ascorbic acid oxidase (see patent document 1); a method for stabilizing an ascorbic acid oxidase by maintaining an ascorbic acid oxidase under lyophilization in the presence of an N-substituted taurine buffer (see patent document 2); a method for stabilizing an ascorbic acid oxidase by allowing an ascorbic acid oxidase to coexist with one or more selected from skim milk, lactose, sucrose, and soluble starch (see patent document 3); a method for stabilizing an ascorbic acid oxidase in a solution state by chemically binding an ascorbic acid oxidase to a water-soluble carrier selected from bovine serum albumin, dextran, and polyethylene glycol (see patent document 4); a method for stabilizing an ascorbic acid oxidase by adding one or more kind of pyruvic acid (and salts thereof) therein (see patent document 5); a method for stabilizing an ascorbic acid oxidase by adding a sugar alcohol to a solution containing an ascorbic acid oxidase (see patent document 6); a method for stabilizing an ascorbic acid oxidase by allowing the ascorbic acid oxidase to coexist with a substance selected from 2-methyl-4-isothiazolin-3-one, 5-chloro-2-methyl-4-isothiazolin-3-one, 1,2-benzisothiazolin-3-one, and salts thereof (see patent document 7); a method for stabilizing an ascorbic acid oxidase in a dried state by allowing the ascorbic acid oxidase to coexist with a protein degradation product (see patent document 8); a method for stabilizing an ascorbic acid oxidase by adding an amino acid and an amino acid salt and/or an oligopeptide (see patent document 9), and the like.

PRIOR ART DOCUMENTS

Patent Documents

Patent Document 1: Japanese Patent Publication No. 8-015430
Patent Document 2: Japanese unexamined Patent Application Publication No. 4-066087
Patent Document 3: Japanese unexamined Patent Application Publication No. 5-244948
Patent Document 4: Japanese unexamined Patent Application Publication No. 6-062846
Patent Document 5: Japanese unexamined Patent Application Publication No. 2002-233363
Patent Document 6: Japanese unexamined Patent Application Publication No. 2003-116539
Patent Document 7: Japanese unexamined Patent Application Publication No. 2004-105025
Patent Document 8: Japanese unexamined Patent Application Publication No. 2005-114368
Patent Document 9: Japanese unexamined Patent Application Publication No. 2007-228842

SUMMARY OF THE INVENTION

Problems to be Solved by the Invention

An object of the present invention is to provide a method for stabilizing an ascorbic acid oxidase, a method for preserving an ascorbic acid oxidase, and a stabilized composition of an ascorbic acid oxidase, suitable for long-term preservation.

Means to Solve the Problems

As a result of intensive studies to solve the above problem, the present inventors have found that an ascorbic acid oxidase is stably maintained by allowing the ascorbic acid oxidase to coexist with nitrous acid or a salt thereof, or a nitrous acid ester in an aqueous medium, thereby completing the present invention. Thus, the present invention relates to the following [1] to [3]:

[1] A method for stabilizing an ascorbic acid oxidase, which comprises allowing the ascorbic acid oxidase to coexist with nitrous acid or a salt thereof, or a nitrous acid ester in an aqueous medium;

[2] A method for preserving an ascorbic acid oxidase, which comprises allowing the ascorbic acid oxidase to coexist with nitrous acid or a salt thereof, or a nitrous acid ester in an aqueous medium; and

[3] A stabilized composition of an ascorbic acid oxidase, which comprises the ascorbic acid oxidase being allowed to coexist with nitrous acid or a salt thereof, or a nitrous acid ester in an aqueous medium.

Effect of the Invention

According to the present invention, a method for stabilizing an ascorbic acid oxidase, a method for preserving an ascorbic acid oxidase, and a stabilized composition of an ascorbic acid oxidase, suitable for long-term preservation are provided.

Mode of Carrying Out the Invention

The method for stabilizing an ascorbic acid oxidase according to the present invention is a method which comprises allowing the ascorbic acid oxidase to coexist with nitrous acid or a salt thereof, or a nitrous acid ester in an aqueous medium.

The method for preserving an ascorbic acid oxidase according to the present invention is a method which comprises allowing the ascorbic acid oxidase to coexist with nitrous acid or a salt thereof, or a nitrous acid ester in an aqueous medium.

The stabilized composition of an ascorbic acid oxidase according to the present invention is a composition which comprises the ascorbic acid oxidase being allowed to coexist with nitrous acid or a salt thereof, or a nitrous acid ester in an aqueous medium.

"Stabilization" in the present invention means the enzyme activity of ascorbic acid oxidase is maintained on a long-term preservation of the ascorbic acid oxidase; specifically, it means after an aqueous solution of ascorbic acid oxidase is preserved at 30° C. for 10 days, the activity of an ascorbic acid oxidase after preservation at 30° C. for 10 days is 60% or more of the activity of an ascorbic acid oxidase immediately after the preparation of the aqueous solution of ascorbic acid oxidase. The activity of an ascorbic acid oxidase can be measured, for example, by the following method.

An aqueous solution of ascorbic acid as a substrate for ascorbic acid oxidase (a substrate solution) is prepared. A specimen (x μL) containing an ascorbic acid oxidase is added to a buffer solution (y μL) warmed at 37° C. for 5 minutes in advance, and then the substrate solution (z μL) is added thereto. The absorbance (E1) at 292 nm of the reaction solution at 2 minutes after adding the substrate solution and the absorbance (E2) at 292 nm of the reaction solution at 3 minutes after adding the substrate solution are measured, and the activity of ascorbic acid oxidase in the specimen is calculated by the following equation (I).

[Expression 1]

$$\text{Activity of an ascorbic acid oxidase (U/mL)} = (E1-E2)/2.2 \ast (x+y+z)/x \quad (I)$$

The stabilization of an ascorbic acid oxidase can be evaluated, for example, by the following method. Specimen A prepared by adding an ascorbic acid oxidase and nitrous acid or a salt thereof, or a nitrous acid ester to a buffer solution containing bovine serum albumin (BSA) is used as a specimen containing an ascorbic acid oxidase to prepare specimen $A_{(immediately\ after\ preparation)}$ immediately after preparation and specimen $A_{(after\ preservation)}$ after preserving the specimen $A_{(immediately\ after\ preparation)}$ at 30° C. for 10 days. In addition, specimen 'a' containing neither nitrous acid or a salt thereof, nor a nitrous acid ester, prepared by adding only an ascorbic acid oxidase to a buffer solution containing bovine serum albumin (BSA) is used to prepare specimen $a_{(immediately\ after\ preparation)}$ immediately after preparation and specimen $a_{(after\ preservation)}$ after preserving the specimen $a_{(immediately\ after\ preparation)}$ at 30° C. for 10 days.

The specimen $A_{(immediately\ after\ preparation)}$ is used as a specimen to calculate the activity $V_{A(immediately\ after\ preparation)}$ of ascorbic acid oxidase in the specimen $A_{(immediately\ after\ preparation)}$ by the aforementioned method for measuring activity of an ascorbic acid oxidase. Similarly, the specimen $A_{(after\ preservation)}$ specimen $a_{(immediately\ after\ preparation)}$, or specimen $a_{(after\ preservation)}$ is used in place of the specimen $A_{(immediately\ after\ preparation)}$ as a specimen to calculate each of the activity $V_{A(after\ preservation)}$, $V_{a(immediately\ after\ preparation)}$, and $V_{a(after\ reservation)}$ of ascorbic acid oxidase in each of the corresponding specimens. The residual ratio of ascorbic acid oxidase activity in the specimen A is calculated by the following equation (II).

[Expression 2]

$$\text{Residual ratio (\%)} = V_{A(after\ preservation)}/V_{A(immediately\ after\ preparation)} \ast 100 \quad (II)$$

Similarly the residual ratio of ascorbic acid oxidase activity in the specimen 'a' is calculated by the following equation (III).

[Expression 3]

$$\text{Residual ratio (\%)} = V_{a(after\ preservation)}/V_{a(immediately\ after\ preparation)} \ast 100 \quad (III)$$

In case the residual ratio of ascorbic acid oxidase activity in the specimen A calculated from the equation (II) described above is 60% or more and higher than the residual ratio of ascorbic acid oxidase activity in the specimen 'a' calculated from the equation (III) described above, it can be evaluated that the ascorbic acid oxidase has been stabilized by nitrous acid or a salt thereof, or a nitrous acid ester.

The ascorbic acid oxidase according to the present invention is an enzyme classified as EC1.10.3.3 and an enzyme catalyzing any of the following reactions.

$$\text{L-ascorbic acid} + \tfrac{1}{2}O_2 \rightarrow \text{dehydroascorbic acid} + H_2O \quad (1)$$

Examples of the ascorbic acid oxidase catalyzing the reaction include an ascorbic acid oxidase derived from a plant such as cucumber and squash.

$$\text{L-ascorbic acid} + O_2 \rightarrow \text{dehydroascorbic acid} + H_2O_2 \quad (2)$$

Examples of the ascorbic acid oxidase catalyzing the reaction include an ascorbic acid oxidase derived from a microorganism such as the genera *Trichoderma, Mortierella*, and *Eupenicillium*.

The ascorbic acid oxidase catalyzing the reaction of (1) above can be obtained, for example, from Wako Pure Chemical Industries Ltd., Asahi Kasei Pharma Corporation, Roche Diagnostics K.K., and Toyobo Co., Ltd. A chemically modified ascorbic acid oxidase can also be used as the ascorbic acid oxidase catalyzing the reaction of (1) above, and the chemically modified ascorbic acid oxidase can be obtained, for example, from Roche Diagnostics K.K. The ascorbic acid oxidase catalyzing the reaction of (2) above can be obtained, for example, from Amano Enzyme Inc.

According to the present invention, the aqueous medium is not particularly limited so long as it is an aqueous medium which can keep an ascorbic acid oxidase stable; examples thereof include a deionized water, a distilled water, and a buffer solution, and is preferred a buffer solution. According to the present invention, the concentration of ascorbic acid oxidase in the aqueous medium is usually 0.1 to 100 U/mL. A buffer having a buffer capacity in the pH region where an ascorbic acid oxidase can be kept stable is preferred as a buffer solution; examples thereof include a phosphate buffer solution, a borate buffer solution, and a Good's buffer solution. Examples of the Good's buffer used in the Good's buffer solution include 2-morpholinoethanesulfonic acid (MES), tris(hydroxymethyl)aminomethane (Tris), bis(2-hydroxyethyl)iminotris(hydroxymethyl)methane (Bis-Tris), N-(2-acetamido)iminodiacetic acid (ADA), piperazine-N,N'-bis(2-ethanesulfonic acid) (PIPES), N-(2-acetamido)-2-aminoethanesulfonic acid (ACES), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), piperazine-N,N'-bis(2-hydroxypropanesulfonic acid) (POPSO), N-[tris(hydroxymethyl)methyl]glycine (Tricine), N,N-bis(2-hydroxyethyl)glycine (Bicine), N-tris(hydroxymethyl)methyl-3-aminopropanesulfonic acid (TAPS), N-cyclohexyl-2-aminoethanesulfonic acid (CHES), and N-cyclohexyl-3-aminopropanesulfonic acid (CAPS).

According to the present invention, an ascorbic acid oxidase is usually preserved in an aqueous medium having a pH of 5 to 9 and preferably preserved in an aqueous medium having a pH of 6 to 8.

The nitrous acid or a salt thereof according to the present invention is not particularly limited so long as it stabilizes an ascorbic acid oxidase. Examples of the salt of nitrous acid include a lithium salt, a sodium salt, a potassium salt, an ammonium salt, a calcium salt, and a magnesium salt.

The nitrous acid ester according to the present invention is not particularly limited so long as it is a nitrous acid ester which can stabilize the ascorbic acid oxidase. Examples of the nitrous acid ester include alkyl nitrite. Examples of the alkyl nitrite include methyl nitrite, ethyl nitrite, propyl nitrite, butyl nitrite, pentyl nitrite, and isopentyl nitrite.

The concentration of the nitrous acid or a salt thereof, or a nitrous acid ester according to the present invention in the aqueous medium is not particularly limited so long as it is a concentration which can stabilize an ascorbic acid oxidase; the concentration is usually 0.01 to 100 mmol/L, preferably 0.05 to 50 mmol/L.

The method for preserving an ascorbic acid oxidase according to the present invention is a method for preservation which comprises allowing the ascorbic acid oxidase to coexist with nitrous acid or a salt thereof, or a nitrous acid ester in an aqueous medium. Examples of ascorbic acid oxidase and the concentration thereof and the nitrous acid or a salt thereof, or a nitrous acid ester and the concentration thereof used in the method for preserving an ascorbic acid oxidase according to the present invention are the same as those used in the method for stabilizing an ascorbic acid oxidase. The preservation period in the method for preserving an ascorbic acid oxidase according to the present invention is not particularly limited so long as it is a period which enables to preserve an ascorbic acid oxidase stably; the period is usually 1 to 2 years. The preservation temperature in the method for preserving an ascorbic acid oxidase according to the present invention is also not particularly limited so long as it is a temperature which enables to preserve an ascorbic acid oxidase stably; the temperature is usually −5 to 45° C., preferably 0 to 30° C., particularly preferably 2 to 10° C.

In the method for preserving an ascorbic acid oxidase according to the present invention, a surfactant, a preservative, a protein, and the like in addition to nitrous acid or a salt thereof, or a nitrous acid ester may coexist with an ascorbic acid oxidase. Examples of the surfactant include a nonionic surfactant, a cationic surfactant, an anionic surfactant, and an amphoteric surfactant. Examples of the preservative include an azide and a chelator. Examples of the azide include sodium azide. Examples of the chelator include ethylenediaminetetraacetic acid (EDTA) or a salt thereof.

Examples of the salt include a sodium salt and a potassium salt. Examples of the protein include albumin; examples of albumin include BSA.

The stabilized composition of an ascorbic acid oxidase according to the present invention may comprise components usually comprised in a reagent and a kit used in a method for measuring a component to be measured based on a hydrogen peroxide measuring system, in addition to an ascorbic acid oxidase and nitrous acid or a salt thereof, or a nitrous acid ester. Examples of the component to be measured include total cholesterol (TC), cholesterol in high density lipoprotein (HDL-C), cholesterol in low density lipoprotein (LDL-C), cholesterol in very low density lipoprotein (VLDL-C), cholesterol in remnant-like lipoprotein (RLP-C), free cholesterol (FC), triglyceride, uric acid, phospholipid, and glycated protein.

For example, the reagent and kit used in a method for measuring cholesterol (TC, HDL-C, LDL-C, VLDL-C, or RLP-C) comprise cholesterol esterase, cholesterol oxidase, peroxidase, and an oxidative-coloring chromogen in addition to an ascorbic acid oxidase and nitrous acid or a salt thereof, or a nitrous acid ester, and the reagent and kit used in a method for measuring triglyceride comprise lipase, glycerol kinase, ATP, glycerol 3-phosphate oxidase, peroxidase, and an oxidative-coloring chromogen in addition to an ascorbic acid oxidase.

Examples of the oxidative-coloring chromogen include a leuco chromogen and an oxidative-coupling chromogen.

The leuco chromogen has a function of reacting with hydrogen peroxide in the presence of a peroxidase to form a dye in itself. Examples of the leuco chromogen include tetramethylbenzidine, o-phenylenediamine, 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), N-(carboxymethylaminocarbonyl)-4,4'-bis(dimethylamino) diphenylamine sodium salt (DA-64), 10-N-carboxymethylcarbamoyl-3,7-bis(dimethylamino)-10H-phenothiazine sodium salt (DA-67), 4,4'-bis(dimethylamino)diphenylamine, and bis[3-bis(4-chlorophenyl)methyl-4-dimethylaminophenyl]amine (BCMA).

The oxidative coupling-coloring chromogen has a function of reacting with hydrogen peroxide in the presence of a peroxidase to form a dye. In this reaction to form a dye, a combination of a pair of oxidative coupling-coloring chromogens is used. Examples of the combination of the pair of oxidative coupling-coloring chromogen include a combination of a coupler and an aniline and a combination of a coupler and a phenol.

Examples of the coupler include 4-aminoantipyrine (4-AA) and 3-methyl-2-benzothiazolinone hydrazine.

Examples of the aniline include N-(3-sulfopropyl)aniline, N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl- N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-di(3-sulfopropyl)-3,5-dimethoxyaniline, N-ethyl- N- (3-sulfopropyl)-3-methoxyaniline, N-ethyl-N-(3- sulfopropyl)aniline, N-ethyl-N- (3-sulfopropyl)-3,5- dimethoxyaniline, N-(3-sulfopropyl)-3,5- dimethoxyaniline, N-ethyl-N-(3-sulfopropyl)-3,5- dimethylaniline, N-ethyl-N-(2-hydroxy-3-sulfopropyl)-3-methoxyaniline, N-ethyl-N-(2-hydroxy-3-sulfopropyl) aniline, N-ethyl-N-(3-methylphenyl)-N'-succinylethylenediamine (EMSE), N-ethyl-N-(3- methylphenyl)-N'-acetylethylenediamine, and N-ethyl-N-(2-hydroxy-3-sulfopropyl)-4-fluoro-3,5-dimethoxyaniline (F-DAOS).

Examples of the phenol include phenol, 4-chlorophenol, 3-methylphenol, and 3-hydroxy-2,4,6-triiodobenzoic acid (HTIB).

The stabilized composition of an ascorbic acid oxidase according to the present invention may comprise the surfactant, preservative, and protein mentioned above.

Hereinbelow, the present invention is described more specifically according to Examples, but these Examples are not intended to limit the scope of the present invention in any way. It should be noted that reagents and enzymes from the following manufacturers were used in Examples, Comparative Examples, and Test Examples.

MOPS (manufactured by Dojindo Laboratories), BSA (manufactured by Millipore Corporation), potassium dihydrogen phosphate (manufactured by Junsei Chemical Co., Ltd.), sodium acetate (manufactured by Kanto Chemical Co., Inc.), ascorbic acid (manufactured by Nacalai Tesque, Inc.), sodium nitrite (manufactured by Junsei Chemical Co., Ltd.), potassium nitrite (manufactured by Junsei Chemical Co., Ltd.), ethyl nitrite (manufactured by Tokyo Chemical Industry Co., Ltd.), ascorbic acid oxidase (manufactured by Asahi Kasei Pharma Corporation), and chemically modified ascorbic acid oxidase (manufactured by Roche Diagnostics K.K.).

EXAMPLES

Example 1

The effects of a salt of nitrous acid and a nitrous acid ester for stabilizing an ascorbic acid oxidase were evaluated by the following method.

(1) Specimen

Specimen A (specimens A0 to A4) and specimen B (specimens B0 to B4) consisting of the following compositions were prepared.

| <Specimen A (specimens A0 to A4)> | |
|---|---|
| MOPS (pH 7.0) | 20 mmol/L |
| BSA | 4 g/L |
| Chemically modified ascorbic acid oxidase | 4 kU/L |

A salt of nitrous acid or a nitrous acid ester (see Table 1, specimen A0 containing neither salt of nitrous acid nor a nitrous acid ester)

| <Specimen B (specimens B0 to B4)> | |
|---|---|
| MOPS (pH 7.0) | 20 mmol/L |
| BSA | 4 g/L |
| Ascorbic acid oxidase | 4 kU/L |

A salt of nitrous acid or a nitrous acid ester (see Table 1, specimen B0 containing neither salt of nitrous acid nor a nitrous acid ester)

(2) Buffer Solution for Measuring of Ascorbic Acid Oxidase Activity

A buffer solution for measuring ascorbic acid oxidase activity, consisting of the following composition was prepared.

| | |
|---|---|
| Potassium dihydrogen phosphate (pH 6.0) | 67 mmol/L |
| Sodium acetate | 67 mmol/L |
| BSA | 1 g/L |

(3) Substrate Solution of Ascorbic Acid Oxidase

An ascorbic acid aqueous solution (3 g/L) was used as a substrate solution of ascorbic acid oxidase.

(4) Ascorbic Acid Oxidase Activity in Specimen Immediately After Preparation

The reagent (3 mL) for measuring ascorbic acid oxidase activity in above (2) was added to a reaction cuvette and incubated at 37° C. for 5 minutes. The specimen A1 (0.04 mL) was added thereto, and then the substrate solution for ascorbic acid oxidase (0.1 mL) in above (3) was added to start reaction. The absorbance (E1) at 292 nm of the reaction solution at 2 minutes after reaction and the absorbance (E2) at 292 nm of the reaction solution at 3 minutes after reaction were measured, and activity $V_{A1(immediately\ after\ preparation)}$ of an ascorbic acid oxidase in the specimen A1 was determined by the aforementioned equation (I).

(5) Ascorbic Acid Oxidase Activity in Specimen After Preservation at 30° C. for 10 Days Activity $V_{A1(after\ preservation)}$ of an ascorbic acid oxidase in the specimen A1 after preservation at 30° C. for 10 days was determined in the same way as in above (4) except for using the specimen A1 after preservation at 30° C. for 10 days in place of the specimen A1 immediately after preparation.

(6) Residual Ratio of Ascorbic Acid Oxidase Activity in Specimen after Preservation at 30° C. for 10 Days The residual ratio of ascorbic acid oxidase activity in the specimen A1 after preservation at 30° C. for 10 days relative to activity of an ascorbic acid oxidase in the specimen A1 immediately after preparation was determined by the aforementioned equation (II) from $V_{A1(immediately\ after\ preparation)}$ determined in above (4) and $V_{A1(after\ preservation)}$ determined in above (5). The results are shown in Table 1.

In the same way as in above (1) to (6) except for using each of the specimens A2 to A4 and B1 to B4 in place of the specimen A1 as a specimen, the residual ratio of ascorbic acid oxidase activity in each of the specimens after preservation at 30° C. for 10 days relative to ascorbic acid oxidase in each of the specimens immediately after preparation was determined. The results are shown in Table 1.

In the same way as in above (1) to (6) except for using each of the specimens A0 and B0 in place of the specimen A1 and using the aforementioned equation (III) in place of the aforementioned equation (II), the residual ratio of ascorbic acid oxidase activity in each specimen after preservation at 30° C. for 10 days relative to ascorbic acid oxidase activity in each specimen immediately after preparation was further determined. The results are shown in Table 1.

TABLE 1

| Specimen | Salt of Nitrous Acid or Ester of Nitrous Acid (Concentration) | Residual Ratio (%) |
|---|---|---|
| A0 | — | 52 |
| A1 | Sodium Nitrite (7 mmol/L) | 72 |

TABLE 1-continued

| Specimen | Salt of Nitrous Acid or Ester of Nitrous Acid (Concentration) | Residual Ratio (%) |
|---|---|---|
| A2 | Sodium Nitrite (14 mmol/L) | 72 |
| A3 | Potassium Nitrite (7 mmol/L) | 68 |
| A4 | Ethyl Nitrite (7 mmol/L) | 70 |
| B0 | — | 48 |
| B1 | Sodium Nitrite (7 mmol/L) | 87 |
| B2 | Sodium Nitrite (14 mmol/L) | 89 |
| B3 | Potassium Nitrite (7 mmol/L) | 85 |
| B4 | Ethyl Nitrite (7 mmol/L) | 83 |

It is apparent from Table 1 that the residual ratio of ascorbic acid oxidase activity was 60% or more under the coexistence of a salt of nitrous acid or a nitrous acid ester compared to that under the absence of a salt of nitrous acid or a nitrous acid ester even in the case where a chemically modified ascorbic acid oxidase was used as an ascorbic acid oxidase (A0 to A4) or even in the case where a non-modified ascorbic acid oxidase was used (B0 to B4). In contrast, the residual ratio thereof was less than 60% under the absence of a salt of nitrous acid or a nitrous acid ester. Thus, it proved that the coexistence of a salt of nitrous acid or a nitrous acid ester with an ascorbic acid oxidase in an aqueous medium stabilizes the ascorbic acid oxidase.

INDUSTRIAL APPLICABILITY

According to the present invention, a method for stabilizing an ascorbic acid oxidase, a method for preserving an ascorbic acid oxidase, and a stabilized composition of an ascorbic acid oxidase are provided. The method for stabilizing an ascorbic acid oxidase, the method for preserving an ascorbic acid oxidase, and the stabilized composition of an ascorbic acid oxidase according to the present invention are useful for clinical diagnosis and the like.

The invention claimed is:

1. A method for stabilizing an ascorbic acid oxidase, which comprises allowing the ascorbic acid oxidase to coexist at −5 to 45° C. for at least 10 days with nitrous acid or a salt thereof, or a nitrous acid ester in an aqueous medium, wherein
   the salt is selected from the group consisting of a lithium salt, a sodium salt, a potassium salt, an ammonium salt, a calcium salt and a magnesium salt, and
   the nitrous acid ester is selected from the group consisting of methyl nitrite, ethyl nitrite, propyl nitrite, butyl nitrite, pentyl nitrite and isopentyl nitrite.

2. A method for preserving an ascorbic acid oxidase, which comprises allowing the ascorbic acid oxidase to coexist at −5 to 45° C. for at least 10 days with nitrous acid or a salt thereof, or a nitrous acid ester in an aqueous medium, wherein
   the salt is selected from the group consisting of a lithium salt, a sodium salt, a potassium salt, an ammonium salt, a calcium salt and a magnesium salt, and
   the nitrous acid ester is selected from the group consisting of methyl nitrite, ethyl nitrite, propyl nitrite, butyl nitrite, pentyl nitrite and isopentyl nitrite.

* * * * *